United States Patent
Krull et al.

(10) Patent No.: US 9,610,314 B1
(45) Date of Patent: Apr. 4, 2017

(54) METHOD FOR CONTROLLING POULTRY COCCIDIOSIS

(71) Applicants: Werner Krull, Lucerne (CH); Elie Barbour, Brookhaven, GA (US)

(72) Inventors: Werner Krull, Lucerne (CH); Elie Barbour, Brookhaven, GA (US)

( * ) Notice: Subject to any disclaimer, the term of this patent is extended or adjusted under 35 U.S.C. 154(b) by 0 days.

(21) Appl. No.: 15/228,969

(22) Filed: Aug. 4, 2016

(51) Int. Cl.
| | | |
|---|---|---|
| *A61K 36/00* | (2006.01) | |
| *A61K 36/537* | (2006.01) | |
| *A61K 31/05* | (2006.01) | |
| *A61K 36/61* | (2006.01) | |
| *A61K 36/534* | (2006.01) | |
| *A23K 50/75* | (2016.01) | |
| *A23K 20/195* | (2016.01) | |
| *A23K 20/111* | (2016.01) | |
| *A23K 20/10* | (2016.01) | |

(52) U.S. Cl.
CPC ............ *A61K 36/537* (2013.01); *A23K 20/10* (2016.05); *A23K 20/111* (2016.05); *A23K 20/195* (2016.05); *A23K 50/75* (2016.05); *A61K 31/05* (2013.01); *A61K 36/534* (2013.01); *A61K 36/61* (2013.01)

(58) Field of Classification Search
None
See application file for complete search history.

*Primary Examiner* — Qiuwen Mi
(74) *Attorney, Agent, or Firm* — Gulf Coast Intellectual Property Group

(57) ABSTRACT

A method of controlling poultry coccidiosis in chickens through the application of a formulated disinfectant and administration of a formulated coccidiostat provided in drinking water for the chickens. The method of the present invention includes formulation of a phenolic based disinfectant wherein the disinfectant includes phenol derivatives, organic solvents, organic acids, inorganic acids and an anionic surfactant. The disinfectant is applied to the surface of the area where chickens will be raised prior to placement of the chickens. A coccidiostat is formulated wherein the coccidiostat includes a water extract of *Salvia Libonitica*, eucalyptus oil and peppermint oil. The coccidiostat is diluted in drinking water that is provided to the chickens during the first thirty five days of raising. The drinking water having the coccidiostat diluted therein is provided intermittently a total of fifteen times during the initial thirty-five day raising period.

20 Claims, 2 Drawing Sheets

| Ingredient | Percentage |
|---|---|
| Phenol Derivatives | 5-30% |
| Organic Solvents | 10-30% |
| Organic/Inorganic Acids | 20-40% |
| Anionic Surfactant | 5-10% |

Fig. 1

| Ingredient | Percentage |
|---|---|
| Water Extract of Salvia Libonitica | 2-10% |
| Eucalyptus Oil | 5-15% |
| Peppermint Oil | 4-12% |

Fig. 2

METHOD FOR CONTROLLING POULTRY COCCIDIOSIS

FIELD OF THE INVENTION

The present invention relates generally to poultry disease control, more specifically but not by way of limitation, a method for controlling poultry coccidiosis and further enhancing growth of young chickens utilizing a method of combining a disinfectant and a plant-derived supplement to drinking water.

BACKGROUND

Chicken is one of the most consumed meats wherein just in the United States alone some eight billion chickens per year are consumed. In order to meet this high demand most poultry are provided with antibiotics growth promoters and other chemicals in order to accelerate the growth cycle. Poultry coccidiosis is quite common during raising of chickens. Poultry coccidiosis is a common protozoan disease in domestic birds characterized by enteritis and bloody diarrhea. When poultry is infected with the aforementioned condition bloody feces, ruffled feathers and reduced head size are also observed. Sources of the aforementioned condition include but are not limited to environmental coccidial oocysts and other economic microbes. The control of multiplication of coccidial organisms presents a challenge for poultry farmers. It is common in the field to treat the poultry with synthetic coccidiostats in order to control the aforementioned condition. One issue with the aforementioned is that many consumers dislike poultry that is contaminated with synthetic coccidiostats and other antibiotic growth promoters.

Another issue with the current method of poultry farming is the significant utilization of antibiotic growth promoters. Additionally, no current method of poultry raising includes a technique for controlling poultry coccidiosis and further provide enhanced growth of the chickens. A method of enhancing growth promotion through utilization of a dual application of an effective disinfectant and a natural herbal supplement does not currently exist. The providing of a method of for controlling of poultry coccidiosis and enhancement of growth in poultry without the utilization of synthetic coccidiostats is desirable as numerous consumer groups have rejected poultry products that are contaminated with synthetic coccidiostats.

Accordingly, there is a need for a method of raising poultry that utilizes a method of providing a disinfectant and a natural coccidiostat that provides growth promotion and effective removal of environmental oocysts of *Eimeria* spp. in addition to a wide spectrum of other bacteria and viruses typically found on a farm.

SUMMARY OF THE INVENTION

It is the object of the present invention to provide a method to substantially control the spread of poultry coccidiosis through a dual application of an effective disinfectant combined with a plant-derived drinking water supplement.

Another object of the present invention is to provide a method that eliminates the environmental oocysts of *Eimeria* spp. wherein a disinfectant is applied to surfaces of the farm prior to the farm being stocked with day old chicks.

A further object of the present invention is to provide a method of controlling poultry coccidiosis that utilizes a disinfectant composition based on phenol derivatives, organic solvent, organic acids, inorganic acids and an anionic surfactant.

Still another object of the present invention is to provide a method of controlling bacteria and viruses on a chicken farm and further inhibiting the spread of particular diseases amongst livestock such as but not limited to poultry wherein the method further includes intermittent administration to the livestock a supplemented drinking water.

An additional object of the present invention is to provide a method of controlling poultry coccidiosis and enhancing growth promotion wherein the supplemented drinking water includes a blend of essential oils of *eucalyptus* and peppermint emulsified in a water extract of *Salvia Libonitica*.

Yet a further object of the present invention is to provide a method of controlling poultry coccidiosis through a dual application of a disinfectant and supplemented drinking water wherein the supplemented drinking water can further include alternative plant derived components such as but not limited to Isopulegol, Thymol, Eugenol, Carvone, Carvacrol, Cineol, Carveol and Cinnamaldehyde.

Another object of the present invention is to provide a method of controlling environmental coccidial oocysts and other microbes on a farm and further enhancing the growth promotion of chickens wherein the supplemented water is intermittently administered during the first six weeks of the life of the poultry.

To the accomplishment of the above and related objects the present invention may be embodied in the form illustrated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Description and appended claims when taken in conjunction with the accompanying Drawings wherein:

FIG. 1 is a table of the disinfectant composition of the present invention; and FIG. 2 is a table of the coccidiostat of the present invention.

DETAILED DESCRIPTION

Figure 3:
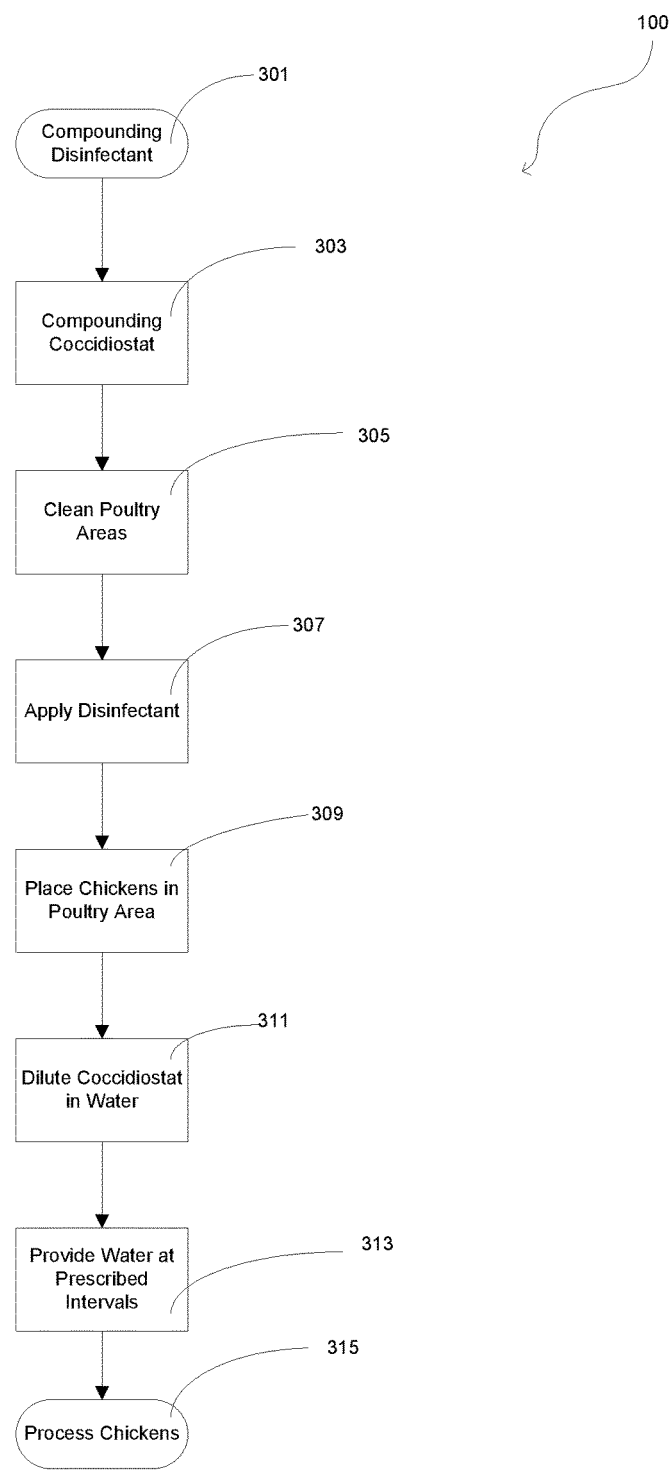
FIG. 3 is a flow chart of an exemplary method of use of the present invention.

Referring now to the drawings submitted herewith, wherein various elements depicted therein are not necessarily drawn to scale and wherein through the views and figures like elements are referenced with identical reference numerals, there is illustrated a method for controlling poultry coccidiosis 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to FIG. 1 the preferred embodiment of the disinfectant of the present invention is detailed therein. The preferred embodiment of the disinfectant of the present invention includes phenol derivatives comprising within a range of 5 to 30 percent of the disinfectant. It is contemplated within the scope of the present invention that various phenolic compounds could be utilized such as but not limited to hexachlorophene or chloroxylenol. It is contemplated within the scope of the present invention that the composition of the disinfectant of the present invention could include alternate phenolic compounds and/or derivatives. The disinfectant of the present invention further includes 10 to 30 percent of organic solvents. Further, in the preferred embodiment of the present invention the disinfectant includes 20 to 40 percent of organic/inorganic acids. Additionally, the disinfectant of the present invention includes 5 to 10 percent of an anionic surfactant. It is further contemplated within the scope of the present invention that the disinfectant of the present invention could further include keratolytyic agents as additives. In the preferred method of use as further discussed herein, the disinfectant is applied to farm surfaces prior to the arrival of day old chicks. While a range of dilution is possible, good results have been achieved utilizing a 3 to 5 percent dilution of the disclosed disinfectant wherein an optimum dilution of 3 percent is preferred. The preferred application rate of the disclosed disinfectant is a rate of 200 to 400 milliliters dilution per square meter. It is contemplated within the scope of the present invention that the application rate could be varied to meet demands of certain environments.

Referring to FIG. 2 herein, a table of the coccidiostat of the present invention is disclosed. The coccidiostat of the present invention contains a blend of oils emulsified in a water extract of *Salvia Libonitica*. As further discussed herein the coccidiostat of the present invention is administered to poultry during the initial thirty five days of raising at intermittent intervals. The water extract of *Salvia Libonitica* is prepared in a ratio of plant leaves to water of 1:5, wherein a range of preparation of 1:3 to 1:8 is acceptable for the present invention. The coccidiostat of the present invention includes a composition of 2-10 percent water extract of *Salvia Libonitica*, 5-15 percent *eucalyptus* oil and 4-12 percent of peppermint oil. It is contemplated within the scope of the present invention that the coccidiostat of the present invention could include alternate levels of the aforementioned components. The coccidiostat of the present invention is mixed in the drinking water provided to poultry during the raising process. It is preferred within the scope of the present invention that the coccidiostat of the present invention is diluted at one of the following three dilutions in the drinking water provided to poultry: 0.005 percent, 0.010 percent or 0.020 percent. The preferred dilution of the coccidiostat is 0.010. It is further contemplated within the scope of the present invention that additional plant extracts could be added to the preparation of the coccidiostat of the present invention as stimulants to water and feed intake or as an immunopotentiator. These could be added within a range of 1 to 15 percent with a preferred percentage at 10 percent. It is additionally contemplated within the scope of the present invention that the coccidiostat of the present invention could include dyes, wherein the dyes could be added between the ranges of $1.0 \times 10^{-4}$ to $4.0 \times 10^{-4}$ (w/v) wherein a preferred dye addition is at $3.0 \times 10^{-4}$ (w/v).

Examples of use of the method of the present invention wherein the method includes the deployment of the disinfectant of the present invention and the coccidiostat of the present invention as detailed herein. In a first example a trial accomplished on broiler chicken raised in isolation units. The experimental design targeted an evaluation of the method of the present invention wherein a dual application of the disinfectant of the present invention in combination with the coccidiostat of the present invention implemented on a contaminated premises by coccidial oocysts versus an application to another similarly contaminated premises of a conventional disinfectant based on chlorine, and administering intermittently to stocked day-old broiler chicks, raised on the two premises, the same developed natural coccidiostat, described above, at a dilution of 0.02% in drinking water. Details of this design is as follows: Four isolation pens were included to contain 10 experimental day-old broilers per pen. The cleaned surfaces were contaminated with total sporulated Oocysts of 8 *Eimeria* spp. equivalent to $4.0 \times 10^5 /m^2$. The sporulated count of each of the 8 *Eimeria* spp. was equivalent to $5.0 \times 10^4 /m^2$. The 8 *Eimeria* spp. were *E. acervulina, E. brunetti, E. hagani, E. maxima, E. mivati, E. necatrix, E. praecox,* and *E. tenella*. The contaminated surfaces of the two pens were disinfected using a conventional sodium hypochlorite, diluting it, according to manufacturer instructions, up to 0.82%, with an application of 400 ml/m², and a contact time of two hrs. The cleaned surfaces of the other two pens were disinfected with the disinfectant of the present invention with a dilution of 3.0% v/v in water, with an application of 400 ml/m², and a contact time of two hrs. The dried floors of the four pens were covered with wood shavings from the same source. The four pens were stocked at the same time by meat-type chicks, of same breed Ross 308, and originating from the same breeder flock, to ensure that they carry the same average maternal immunity. The birds were vaccinated intra-occularly against NewCastle Disease Virus at an age of 1 and 14 days, and against Infectious Bronchitis Virus and Infectious Bursal Disease Virus at an age of 8 days. All birds in the 4 pens were offered drinking water supplemented with the developed natural coccidiostat (0.02%), intermittently at the ages of 4-6, 10-12, 18-20, 24-26, and 31-33 day-old (total days of treatment were 15). In the other days of rearing, the birds were offered plain drinking water, not supplemented with any product. This trial was terminated at the age of 35 days. The measured parameters in this trial, using duplicate pens per treatment, were the mean cumulative Feed Conversion Ratio (FCR), i.e., the conversion of feed to live weight, the mean cumulative weight gain, and the mean weekly Oocysts output per gram of fecal droppings. The statistical analysis was based on the Completely Randomized Design, applying ANOVA followed by conservative Tukey's test, and statistical difference in means were reported at P<0.05.

Results of Oocyst shedding are shown in Table 3, showing the complete significant absence of this shedding by birds that were subjected to the dual application of the disinfectant of the present invention in their premises, followed by the intermittent supplementation of the coccidiostats of the present invention in their drinking water, compared to the other birds that had the same supplementation of the coccidiostat of the present invention in drinking water but their premises were disinfected a conventional chlorine-based disinfectant.

TABLE 3

Combined approach in reduction of the mean output of coccidial oocysts per gram of broilers' droppings at 14, 21, 28, and 35 days of age.

| | | | Mean Oocyst count × $10^4$/g dropping at ages (days) | | | |
|---|---|---|---|---|---|---|
| Treatment | Disinfectant | Coccidiostat[1] | 14 | 21 | 28 | 35 |
| 1 | Phenolic-derivative based | Water extract And essential oils | $0.0^a$ | $0.0^a$ | $0.0^a$ | $0.0^a$ |
| 2 | Chlorine-based | Water extract And essential oils | $8.1^b$ | $9.3^b$ | $7.5^b$ | $1.6^b$ |

[1]The coccidiostat of the present invention is offered in drinking water (0.02%), intermittently at the following ages: 4-6, 10-12, 18-20, 24-26, and 31-33 day-old (total days of treatment are 15).
$a,b$Means in a column, followed by different alphabetical superscript were significantly different (P < 0.05)

The production parameters of the presently discussed experiment are reported in Table 4, showing the improvement in two production parameters namely, the Mean cumulative weight gain and mean live body weight gain at market age due to the dual application of the disinfectant of the present invention and the coccidiostat of the present invention.

TABLE 4

The method of the present invention and its impact on improving means of weight gain and live body weight of 35 days-old broilers whose pens were differently disinfected:

| Treatment | Disinfectant | Coccidiostat[1] | Mean cumulative weight gain/bird (g) | Mean Live body weight (g) |
|---|---|---|---|---|
| 1 | Phenolic derivate-based | Water extract And essential oils | 1534.3 | 1592.1 |
| 2 | Chlorine-based | Water extract And essential oils | 1485.3 | 1533.2 |

[1]The coccidiostat of the present invention is offered in drinking water (0.02%), intermittently at the following ages: 4-6, 10-12, 18-20, 24-26, and 31-33 day-old (total days of treatment are 15).

Results of deploying the method of the present invention wherein a combination the coccidiostat of the present invention and the disinfectant of the present invention are stated herein below wherein the growth promotion of the chickens as a result of the employment of the method of the present invention was analyzed. An experiment was executed in isolation units, on groups of broiler chicken that were not challenged with any coccidial oocysts, in order to study the growth promotion in chickens administered the coccidiostat of the present invention in comparison to broilers that were deprived of it. This experiment focused on the assessment of the function of the routinely administered coccidiostat of the present invention on growth of broilers in absence of any challenge by coccidial oocysts. Three treatments were established, each having 30 birds, with 6 replicates per treatment and each replicate containing 5 birds. Treatment 1 was offered the coccidiostat of the present invention in drinking water at a dilution of 0.02%, for 5 days, between day 13 to day 17, while Treatment 2 was offered Maxiban, a conventional synthetic coccidiostat in feed, and for the same period, at an inclusion rate of 160 g/100 KG of feed, and Treatment 3 was left without any coccidiostat. Table 5 shows the average daily weight gain and feed conversion rate (FCR) of the three differently treated broilers between the age of 13 to 17 days.

TABLE 5

| Treatment | Coccidiostat | Average daily weight gain/FCR |
|---|---|---|
| 1 | Coccidiostat(of present invention) | $0.074^a$/1.72 |
| 2 | Synthetic coccidiostat | $0.068^b$/1.87 |
| 3 | None | $0.067^b$/1.92 |

$a,b$Averages in a column followed by different alphabet superscripts are significantly different. The data in Table 5 showed the superiority of coccidiostat of the present invention in growth promotion and in obtaining an improved feed conversion to live body weight, compared to broilers offered a conventional synthetic coccidiostat. Additionally the method of the present invention provided superior results to broilers deprived of any coccidiostat.

Referring now to FIG. 3 herein, an overview of the implementation of the method of the present invention is diagrammed therein. In step 301, the disinfectant of the present invention is compounded utilizing the components and percentages thereof as previously discussed herein. As heretofore discussed, the percentages of the components can be altered within the preferred ranges. In step 303, the cocciodiostat of the present invention is compounded in accordance with the earlier discussed techniques. As discussed, the coccidiostat includes a water extract of *Salvia Libonitica* and additional oils emulsified to create the coccidiostat of the present invention that is diluted in the drinking water provided to poultry during the raising phase. Step 305 consists of cleaning the areas in which day-old chick will be placed for raising thereof. The cleaning of the areas such as but not limited to barns or similar areas are executed utilizing standard protocols. In step 307, the disinfectant of the present invention is applied to the areas in which the chickens will be introduced. The disinfectant of the present invention is applied utilizing the heretofore discussed dilution and application rates. Ensuing the application of the disinfectant of the present invention in step 307, the chickens are placed in the areas that have been treated therewith in step 309. In step 311, the coccidiostat of the present invention is diluted in drinking water that will be provided to the chickens during the raising phase. Step 313, the drinking water that has had the coccidiostat of the present invention diluted therein is provided to the chickens. As previously discussed herein, the drinking water having the diluted coccidiostat of the present invention therein is provided through the first thirty-five days of raising wherein the drinking water is provided at the previously provided schedule. In step 315, ensuing the completion of the raising of the chickens the chickens are processed.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A method of controlling disease in chickens and further providing enhancement of the growth thereof comprising the steps of:
    formulating a disinfectant, said disinfectant including a phenol derivative, said phenol derivate being present in said disinfectant between the ranges of five to thirty percent;
    applying said disinfectant to an area in which chickens will be raised;
    formulating a coccidiostat, said coccidiostat having a water extract of *Salvia libanotica*, said water extract of *Salvia libanotica* being present within the coccidiostat within the range of 2 to 10 percent;
    diluting said coccidiostat in drinking water to be provided to chickens;
    administering the drinking water having said coccidiostat diluted therein to chickens during the raising process.

2. The method of controlling disease in chickens and further providing enhancement of the growth thereof as recited in claim 1, wherein the coccidiostat is diluted in the drinking water in at least of the following dilution ratios: 0.005%, 0.010% or 0.020%.

3. The method of controlling disease in chickens and further providing enhancement of the growth thereof as recited in claim 2, wherein the disinfectant is applied to a desired area and wherein the disinfectant is diluted into a solution wherein the dilution ratio of the disinfectant ranges from 3 to 5%.

4. The method of controlling disease in chickens and further providing enhancement of the growth thereof as recited in claim 3, wherein the coccidiostat further includes *eucalyptus* oil between the range of 5 to 15%.

5. The method of controlling disease in chickens and further providing enhancement of the growth thereof as recited in claim 4, wherein the water extract of the *Salvia libanotica* is prepared utilizing a ratio of plant leaves to water within a range of 1:3 to 1:8.

6. The method of controlling disease in chickens and further providing enhancement of the growth thereof as recited in claim 5, wherein the disinfectant is applied to a desired area at an application rate of 200 to 400 ml dilution per square meter.

7. The method of controlling disease in chickens and further providing enhancement of the growth thereof as recited in claim 6, wherein the drinking water having the coccidiostat diluted therein is provided to chickens fifteen times during thirty five days of initial raising.

8. A method of reducing a wide spectrum viral and bacterial microbes in chickens and further providing growth enhancement of the chickens wherein the method comprises the steps of:
    formulating a disinfectant, said disinfectant including a phenol derivative, said phenol derivate being present in said disinfectant between the ranges of five to thirty percent, said disinfectant further including organic solvents, said organic solvents being present in said disinfectant between the ranges of ten to thirty percent;
    diluting said disinfectant, said disinfectant being diluted in a solution wherein the solution will have the disinfectant present therein within the range of three to five percent of the solution;
    applying said solution having said disinfectant diluted therein to an area in which chickens will be raised;
    formulating a coccidiostat, said coccidiostat having a water extract of *Salvia libanotica*, said water extract of *Salvia libanotica* being present within the coccidiostat within the range of 2 to 10 percent;
    diluting said coccidiostat in drinking water to be provided to chickens, said diluting of said coccidiostat in the drinking water being executed such that the coccidiostat is present in the drinking water between the range of 0.005% to 0.020%;
    administering the drinking water having said coccidiostat diluted therein to chickens during the raising process during an initial raising term, the initial raising term being approximately thirty five days.

9. The method reducing a wide spectrum viral and bacterial microbes in chickens and further providing growth enhancement thereof as recited in claim 8, wherein the water extract of the *Salvia libanotica* is prepared utilizing a ratio of plant leaves to water within a range of 1:3 to 1:8.

10. The method reducing a wide spectrum viral and bacterial microbes in chickens and further providing growth enhancement thereof as recited in claim 9, wherein the disinfectant is applied to a desired area at an application rate of 200 to 400 ml dilution per square meter.

11. The method reducing a wide spectrum viral and bacterial microbes in chickens and further providing growth enhancement thereof as recited in claim 10, wherein the step of administering the drinking water is initiated upon the chickens reaching 4 days of age and terminated upon the chickens reaching 33 days of age.

12. The method reducing a wide spectrum viral and bacterial microbes in chickens and further providing growth enhancement thereof as recited in claim 11, wherein the coccidiostat further includes *eucalyptus* oil between the range of 5 to 15%.

13. The method reducing a wide spectrum viral and bacterial microbes in chickens and further providing growth enhancement thereof as recited in claim 12, wherein the coccidiostat further includes peppermint oil, said peppermint oil being present in said coccidiostat between the range of 4 to 12%.

14. The method reducing a wide spectrum viral and bacterial microbes in chickens and further providing growth enhancement thereof as recited in claim 13, wherein the coccidiostat is provided to the chickens fifteen times during the initial raising term.

15. A method of controlling poultry coccidiosis in chickens and further providing growth enhancement of the chickens wherein the method comprises the steps of:
    formulating a disinfectant, said disinfectant including a phenol derivative, said phenol derivate being present in said disinfectant between the ranges of five to thirty percent, said disinfectant further including organic solvents, said organic solvents being present in said disinfectant between the ranges of ten to thirty percent, said disinfectant further including organic and inorganic acids, said organic and inorganic acids being present within the range of 20 to 40%, said disinfectant further including an anionic surfactant;

diluting said disinfectant, said disinfectant being diluted in a solution wherein the solution will have the disinfectant present therein within the range of three to five percent of the solution;

applying said solution having said disinfectant diluted therein to an area in which chickens will be raised, wherein the solution is applied at an application rate of 200 to 400 ml dilution per square meter;

performing a water extract on *Salvia Libanotica*, wherein the water extract of *Salvia libanotica* is executed utilizing a ratio of *Salvia libanotica* leaves to water within the range of 1:3 to 1:8;

formulating a coccidiostat, said coccidiostat having the water extract of *Salvia libanotica*, said water extract of *Salvia libanotica* being present within the coccidiostat within the range of 2 to 10 percent;

diluting said coccidiostat in drinking water to be provided to chickens, said diluting of said coccidiostat in the drinking water being executed such that the coccidiostat is present in the drinking water between the range of 0.005% to 0.020%;

administering the drinking water having said coccidiostat diluted therein to chickens during the raising process during an initial raising term, the initial raising term being approximately thirty five days.

16. The method of controlling poultry coccidiosis in chickens as recited in claim 15, wherein the drinking water is administered to the chickens on the following days of age: 4-6, 10-12, 18-20, 24-26, and 31-33 days of age.

17. The method of controlling poultry coccidiosis in chickens as recited in claim 16, wherein the coccidiostat further includes peppermint oil, said peppermint oil being present in said coccidiostat between the range of 4 to 12%.

18. The method of controlling poultry coccidiosis in chickens as recited in claim 17, wherein the coccidiostat further includes *eucalyptus* oil between the range of 5 to 15%.

19. The method of controlling poultry coccidiosis in chickens as recited in claim 18, wherein said anionic surfactant is present in said disinfectant within the range of 5 to 10%.

20. The method of controlling poultry coccidiosis in chickens as recited in claim 19, wherein said disinfectant further includes keratolytyic agents.

\* \* \* \* \*